United States Patent [19]
Kotzsch et al.

[11] 4,115,427
[45] Sep. 19, 1978

[54] METHOD OF PREPARING SILICON-NITROGEN COMPOUNDS

[75] Inventors: Hans-Joachim Kötzsch; Rüdiger Draese, both of Rheinfelden; Hans-Joachim Vahlensieck, Wehr, all of Germany

[73] Assignee: Dynamit Nobel Aktiengesellschaft, Troisdorf, Germany

[21] Appl. No.: 828,804

[22] Filed: Aug. 29, 1977

[30] Foreign Application Priority Data

Sep. 1, 1976 [DE] Fed. Rep. of Germany ....... 2639286

[51] Int. Cl.² .............................................. C07F 7/10
[52] U.S. Cl. ............................................. 260/448.2 E
[58] Field of Search ................................. 260/448.2 E

[56] References Cited

U.S. PATENT DOCUMENTS

3,530,092   9/1970   Borchert ................... 260/448.2 E X

Primary Examiner—Paul F. Shaver
Attorney, Agent, or Firm—Burgess, Dinklage & Sprung

[57] ABSTRACT

A process for preparing a silicon-nitrogen compound of the formula $(R_3Si)_n NR'_{3-n}$ or $R_2Si(NR'_2)_2$ or $RSi(NR'_2)_3$ or cyclic $(R_2SiNR')_x$ wherein $n$ is 1 or 2 or 3, $R'$ is a hydrogen atom or an alkyl moiety of 1 to 8 carbon atoms or aryl moiety, R represents an alkyl moiety of 1 to 20 carbon atoms or aryl moiety and $x$ is 3 or 4, by contacting a hydrogen silane of the formula $R_{4-y}SiH_y$ where $y$ is 1 or 2 or 3 and R has the above-described meaning with an ammonia or an amine of the formula $NR'_{3-n}H_n$ where $R'$ and $n$ have the above meanings in the presence of a catalyst.

18 Claims, No Drawings

METHOD OF PREPARING SILICON-NITROGEN COMPOUNDS

BACKGROUND OF THE INVENTION

1. Field of the Invention

This invention relates to a method for preparing silicon compounds of the formula $(R_3Si)_n NR'_{3-n}$ or
$R_2Si(NR'_2)_2$ or $RSi(NR'_2)_3$ or
cyclic $+R_2SiNR'+_x$ wherein R, R', n and x have the above-described meanings. More especially this invention relates to the preparation of such silicon-nitrogen compounds by contacting ammonia or an amine with a hydrogen silane of the formula $R_{4-y}SiH_y$.

2. Discussion of the Prior Art

Silazanes prepared by the process herein described have attained commercial importance owing to their use as synthesis adjuvants and protective group reagents in the synthesis of semisynthetic penicillins and cephalosproins, respectively, and other substances, as described, for instance, in U.S. Pat. No. 3,994,545.

The silicon-nitrogen compounds suitable for these purposes have hitherto been prepared by the reaction of chlorosilanes with amines, but several times the amount of amines is needed in order to bind the chloride that is formed as hydrochloride. This unavoidable production of amine hydrochlorides causes additional great disadvantages. The reaction must be performed in dilute solutions in order to keep the pulp stirrable and pumpable. The product must be filtered or centrifuged free of the salt and must then be washed with solvents which, in turn, must be removed by distillation. In spite of washing, large losses of yield result from adsorption onto the salt and the salt wastes have to be disposed of.

SUMMARY OF THE INVENTION

It is an object of this invention, therefore, to provide a simple method for the preparation of such silazanes which is unencumbered by attendant difficult work-up procedures. It is a further object of this invention to provide a process wherein the silazanes are obtained in a virtually quantitative yield at moderate temperatures using readily available catalysts.

Broadly, this invention contemplates a process for the preparation of a silazane of the formula $(R_3Si)_n NR'_{3-n}$ or
$R_2Si(NR'_2)_2$ or $RSi(NR'_2)_3$ or
cyclic $+R_2SiNR'+_x$ wherein n is 1 or 2 or 3, R' is a hydrogen atom or an alkyl moiety of 1 to 8 carbon atoms or aryl moiety, R represents an alkyl moiety of 1 to 20 carbon atoms or aryl moiety and x is 3 or 4, which comprises contacting a hydrogen silane of the formula $R_{4-y}SiH_y$ wherein y is 1 or 2 or 3 and R has the above-described meaning which ammonia or an amine of the formula $NR'_{3-n}H_n$ wherein R' and n have the above-described meanings in the presence of a catalyst. The silazanes are prepared under conditions wherein hydrogen is split-off from the hydrogen silane. Hydrogen is also split-off from the ammonia or the amine.

In accordance with the invention a hydrogen silane is reacted with ammonia or an amine in the presence of a catalyst. Preferably, the catalyst is an element of Group VIII of the Periodic Table of Elements, a salt or a compound thereof.

The moieties R and R' can be branched or unbranched, and can be, if desired, olefinically unsaturated or polyunsaturated alkyl moieties. R and R' can also be cycloalkyl moieties, substituted with alkyl, if desired, such as cyclohexyl moieties, for example. Where R or R' is aryl it is preferably $C_6$-$C_{12}$ aryl, especially phenyl.

Aryl, aralkyl and alkaryl moieties, preferably mononuclear, serve as the aryl moieties, which can be alkyl-substituted on the nucleus, if desired. The side chains or the alkyl substituents, as the case may be, can be branched or unbranched and can be oelfinically monounsaturated or polyunsaturated if desired. The alkyl substituents are preferably those of 1 to 4 carbon atoms.

Amine or ammonia and hydrogen silane are mixed in any desired ratio, but preferably in stoichiometric ratio. This mixture is made to react in the liquid or gaseous state, preferably in the gaseous state, at elevated temperature if desired, in the manner of a heterogeneous catalysis, for example by passing it through the catalyst disposed in a solid bed, the silicon-nitrogen compound plus hydrogen forming, for example, according to the equation:

$$R_{4-y}SiH_y + NR'_{3-n}H_n \rightarrow (R\text{-}Si)_n\text{-}NR'_{3-n} + H_2$$

The products obtainable by the process of the invention are varied depending upon the reactants and the relative amounts of hydrogen silane on the one hand and ammonia or amine on the other. Moreover, in a given hydrogen silane each R group can be the same as the other R groups or it can be different. Similarly, when ammonia or an amine is reacted represented by the formula $NR'_{3-n}H_n$, each R' group can be the same or different from the other R' groups. R' itself can also be hydrogen as in the case of a compound such as methylamine. To further exemplify the process by which the silazanes are prepared there is set forth the equation for the reaction of a simple triorganosilazane with ammonia (R' in both instances being equal to hydrogen):

$$2 R_3SiH + NH_3 \rightarrow (R_3Si)_2NH + H_2$$

The yields are close to 100%. If a stoichiometric ratio of the starting substances is used, the product is obtained in such purity that it can be used without further working up. If one reaction component is present in an excess, the product is worked up by the conventional distillative methods.

Catalysts which are active in accordance with the invention are the elements of Group VIII of the Periodic Table of the Elements, iron, cobalt, nickel, ruthenium, rhodium, palladium, osmium, iridium and platinum in metallic form or in the form of salt-like or complex compounds.

Suitable salt-like or complex compounds are, for example, the salts of the oxygen acids of sulfur or phosphorus, and the halides, carbonates, acetyl acetonates or salts of organic acids.

One form in which the catalysts can be used is the supported form, in which they are supported, for example, on active carbon, aluminum oxide or silicon dioxide of high specific surface area such as, for example, 50 to 1000 m²/g. Porous molded supports, such as those described, for example, in German Pat. No. 1,249,147, are suitable as supporting materials.

The catalysts can also be used in unsupported form, e.g., in solid metallic form, such as for example chips, pellets, packing bodies and the like. The same catalyst metals can also be used as the material of the reactor itself.

The supported catalysts are prepared in a known manner by impregnating the support with a salt or complex salt solution of the catalyst metal, followed by drying and, in some cases, reduction to the metallic form by means of formaldehyde or hydrogen, for example.

By the method of the invention, large numbers of silicon-nitrogen compounds can be prepared, such as, for example, hexamethyldisilazane, N-methylhexamethyldisilazane, N-ethylhexamethyldisilazane, N,N-dimethyltrimethylsilylamine, N,N-diethyltrimethylsilylamine, N-phenyltrimethylsilylamine, hexaethyldisilazane, hexamethylcyclotrisilazane, nonamethylcyclotrisilazane, octamethylcyclotetrasilazane, N,N'-tetramethyldimethylsilyldiamine, N,N'-diphenyldimethylsilyldiamine, Si,Si',Si''-trivinyltrimethylcyclotrisalazane, N,N'-tetramethylvinylmethylsilyldiamine, Si,Si',Si''-triphenyltrimethylcyclotrisilazane, and N,N'-dimethyldiphenylsilyldiamine.

These products are produced by the method of the invention in pure or easily purified form, without the simultaneous formation of wastes.

Hydrogen silanes and amines serve as starting substances. The usable hydrogen silanes are obtainable conventionally from the corresponding organochlorosilanes by chemical or electrochemical hydrogenation; they are, for example, trimethylsilane, dimethylsilane, triethylsilane, diethylsilane, methylvinylsilane, methylphenylsilane, and diphenylsilane.

Amines which can be used in accordance with the invention are, for example, ammonia or primary and secondary amines, such as methylamine, dimethylamine, ethylamine, diethylamine, allylamine, aniline and N-methylaniline.

In a preferred method of procedure, the reaction components are brought into contact with the catalyst particles or bodies which are in the form of a solid bed, without the use of a solvent, the reaction being performed preferably in the gaseous phase.

Basically, however, the reaction can also be performed with an inert solvent. It is best to select as the inert solvents those which are capable of dissolving both the starting substances and the end products. Saturated hydrocarbons, such as gasoline components and the like, are suitable.

A heatable jacketed tube, for example, made of glass, ceramic, steel, nickel or some other catalyst metal, can serve as the reactor, having the catalyst disposed therein preferably in the manner of a solid bed. It is advantageous for the mixture of silane and amine or ammonia, in any desired molar ratio to one another, to be fed downwardly through the solid bed which is preheated to the reaction temperature, whereupon a silicon-nitrogen compound is formed in accordance with the invention, and hydrogen is liberated. Even with very brief times of stay, for example between 0 seconds and 180 seconds (with respect to the empty reactor), a considerable amount of transformation takes place. High transformation rates up to the quantitative transformation and yield are achieved in the time-of-stay range between 3 and 30 minutes. In the case of longer resident times, high, and up to quantitative transformations and yields are also, of course, obtained.

The range of the working temperatures of the method of the invention extends from 0° C to about 280° C.

Preferably the reaction is performed at temperatures above 100° C. As a general rule, higher reaction temperatures require shorter residence times. The reaction can be carried out at sub-atmospheric pressures down to 0.0001 atm or at elevated pressure up to 300 atm although atmospheric pressure is preferred.

A certain influence is also exercised by differences in reactivity among the various hydrogen silanes, amines and catalysts. For the preparation of hexamethyldisilazane by reaction of ammonia with trimethylsilazane it has been found convenient to carry out the process at 160° C employing a residence time of 10 to 15 minutes utilizing a nickel chip catalyst. On the other hand, when aniline is reacted with diphenylsilazane it is convenient to carry the process out at much higher temperature, namely 230° C for a longer period of time, say, 22 to 26 minutes.

It is desirable to perform the reaction with the substantial exclusion of air oxygen and moisture.

The isolation of the silicon-nitrogen compounds prepared in accordance with the invention is accomplished in a simple and known manner by condensation by means of a condenser or a quenching apparatus.

The stochiometric ratio of the compounds to be reacted depend on the desired product. In every case, the hydrogen atom of the hydrogensilane is replaced by the amino group, which optionally can be substituted as indicated. One hydrogen atom of the amine (or ammonia) forms with one hydrogen atom of the hydrogensilane gaseous hydrogen under formation of the silicon — nitrogen liaison. To obtain compounds of the general formula $(R_3Si)_nNR'_{3-n}$ the ratio of hydrogensilane: amine is 2:1, if $n$ to be 2, or 1:1, if $n$ is to be 1. When compounds of the general formula $R_2Si(NR'_2)_2$ are wanted, the ratio of dihydrogensilane: amine is 1:2, and for $RSi(NR'_2)_3$ the ratio is 1:3. Cyclic products are obtained, when the stochiometric ratio of this two compounds is 1:1.

In order to more fully illustrate the nature of the invention and the manner of practicing the same the following examples are presented.

EXAMPLES

The following examples will serve to explain the method of the invention, without limiting same.

EXAMPLE 1

A glass, jacketed tube 900 mm long and 40 mm in diameter, filled with pure nickel lathe chips of about 0.4 mm diameter, is heated by means of a thermostat in the jacket at 168° C and flushed free of air with argon, and then a mixture consisting of trimethylsilane (B.P. 6.7° C) and ammonia is fed downwardly through the tube while the time of stay is varied. The gas emerging at the bottom end of the reactor tube is passed through a water condenser which condenses out the hexamethyldisilazane. The hydrogen is chilled to −62° C, thus yielding about 2% of liquid product, and then removed for further use.

The following table shows the yields of hexamethyldisilazane obtained at 168° C and various times of stay:

| Time of stay* at 168° C on nickel catalyst | Yield of Hexamethyldisilazane | Transformation |
|---|---|---|
| 2'10" | 98.8% | 84.2% |
| 6'35" | 92.2% | 92.1% |

-continued

| Time of stay* at 168° C on nickel catalyst | Yield of Hexamethyldi-silazane | Transformation |
|---|---|---|
| 12' | 99.3% | 95.4% |
| 15' | 99.2% | 96.8% |
| 25' | 99.0% | 98.9% |
| 40' | 99.2% | 98.7% |

*With respect to the empty reactor tube.

6237 g of hexamethyldisilazane with a boiling point of 127° C was prepared in accordance with Example 1. The small amounts of trimethylsilane and ammonia produced in the final distillation were recycled to the reactor. The raw product obtained, however, is of such high purity that it can also be used without distillation.

EXAMPLE 2

The procedure of Example 1 is repeated at 144° C.
The following table shows the yields of hexamethyldisilazane obtained at 144° C and different times of stay.

| Time of stay* at 144° C on nickel catalyst | Yield of Hexamethyldi-silazane | Transformation |
|---|---|---|
| 3'30" | 99.0% | 76.4% |
| 10'10" | 99.4% | 88.1% |
| 20' | 99.8% | 92.1% |
| 30' | 99.1% | 93.8% |

*With respect to the empty reaction tube.

EXAMPLE 3

The procedure of Example 1 is repeated at 120° C.
The following table shows the yields of hexamethyldisilazane obtained at 120° C and different times of stay.

| Time of stay* at 120° C on nickel catalyst | Yield of Hexamethyl-disilazane | Transformation |
|---|---|---|
| 4'20" | 98.0% | 69.5% |
| 17'30" | 98.8% | 76.9% |
| 30'18" | 99.0% | 80.4% |

*With respect to the empty reaction tube.

EXAMPLE 4

In the apparatus described in Example 1, at a catalyst temperature of 210° C, with a moisture-free active carbon containing 0.5% of metallic platinum as the catalyst charge (in 4-mm pellets), N-phenyltrimethylsilylamine was obtained with a boiling point of 206° C in a yield of 93.9% from an equimolecular mixture consisting of trimethylsilane and aniline, in a time of stay of 21 minutes.

EXAMPLE 5

In the manner described in Example 1, from a mixture of allylamine (B.P. 58° C) and dimethylsilane (B.P. −20° C) in a molar ratio of 2 : 1, at a catalyst temperature of 176° C and a time of stay of 11 minutes, bis-N,N'-diallyldimethylsilylamine was obtained with a boiling point of 82° C (at 20 Torr), in a yield of 92.6%.

EXAMPLE 6

In a manner similar to Example 1, but with a catalyst charge consisting of γ-aluminum oxide containing 1% palladium (4-mm pellets), bis-N,N-tetramethyldiphenylsilylamine with a boiling point of 139° C (at 1 Torr) was obtained in a yield of 87.8% from a mixture of dimethylamine and diphenylsilane in a molar ratio of 2 : 1, at a catalyst temperature of 280° C and a time of stay of 25 minutes.

EXAMPLE 7

In a manner similar to Example 1, but with the use of steel lathe chips of about 0.3 mm diameter as the catalyst charge, at a catalyst temperature of 190° C and a time of stay of 15 minutes, nonamethylcyclotrisilazane of a boiling point of 233° C (M.P. 33°–34° C), plus a small amount of oligomers, was obtained in a yield of 82.6% from a mixture of methylamine and dimethylsilane used in a molar ratio of 1 : 1.

EXAMPLE 8

In a manner similar to Example 4, at a catalyst temperature of 180° C and a time of stay of 12 minutes, N-ethylhexamethyldisilazane with a boiling point of 162° to 163° C was obtained in a yield of 96.9% from a mixture of trimethylsilane and ethylamine in a molar ratio of 2 : 1.

What we claim is:

1. A process for preparing a silicon-nitrogen compound of the formula $(R_3Si)_n NR'_{3-n}$ or
$R_2Si(NR'_2)_2$ or $RS: (NR'_2)_3$ or
cyclic $+R_2SiNR'+_x$ wherein
  $n$ is 1 or 2 or 3,
  $R'$ is a hydrogen atom, an alkyl moiety of 1 to 8 carbon atoms or an aryl moiety,
  $R$ is an alkyl moiety of 1 to 20 carbon atoms or an aryl moiety,
  $x$ is 3 or 4
which comprises contacting a hydrogen silane of the formula $R_{4-y}SiH_y$ wherein $y$ is 1 or 2 or 3 and R has the above described meaning with ammonia or an amine of the formula $NR'_{3-n}H_n$ wherein R' and $n$ have the above-described meanings in the presence of a catalyst under conditions wherein hydrogen is split-off.

2. A process according to claim 1 wherein the process is carried out at an elevated temperature.

3. A process according to claim 1 wherein the catalyst is an element of Group VIII of the Periodic System or a salt or compound thereof.

4. A process according to claim 1 wherein the catalyst is one wherein the catalyst component is disposed upon a catalyst support.

5. A process according to claim 4 wherein the catalyst support is active carbon, aluminum oxide or silicon dioxide.

6. A process according to claim 1 wherein the hydrogen silane and ammonia or amine are brought in contact with the catalyst particles or bodies present in the form of a solid bed without the use of a solvent.

7. A process according to claim 1 wherein the reaction is conducted in the gas phase.

8. A process according to claim 1 wherein the reaction is carried out at a temperature of between 0° and 280° C.

9. A process according to claim 8 wherein the hydrogen silane is trimethylsilane, dimethylsilane, triethylsilane, diethylsilane, methylvinylsilane, methylphenylsilane or diphenylsilane.

10. A process according to claim 8 wherein the hydrogen silane is reacted with ammonia.

11. A process according to claim 8 wherein the hydrogen silane is reacted with an amine.

12. A process according to claim 11 wherein said amine is a primary or secondary amine.

13. A process according to claim 12 wherein said amine is methylamine, dimethylamine, ethylamine, diethylamine, allylamine, aniline or N-methylaniline.

14. A process according to claim 1 wherein the catalyst comprises nickel.

15. A process according to claim 1 wherein the catalyst comprises metallic platinum.

16. A process according to claim 1 wherein the catalyst comprises palladium.

17. A process according to claim 1 wherein said hydrogen silane is reacted with ammonia or an amine in the presence of a catatlyst selected from the group consisting of iron, cobalt, nickel, ruthenium, rhodium, palladium, osmium and iridium in metallic form or in the form of a salt-like or complex compound.

18. A process according to claim 10 wherein the hydrogen silane is selected from the group consisting of trimethylsilane, dimethylsilane, triethylsilane, diethylsilane, methylvinylsilane, methylphenylsilane and diphenylsilane.

* * * * *

UNITED STATES PATENT AND TRADEMARK OFFICE
CERTIFICATE OF CORRECTION

PATENT NO. : 4,115,427
DATED : September 19, 1978
INVENTOR(S) : Kötzsch et al.

It is certified that error appears in the above—identified patent and that said Letters Patent are hereby corrected as shown below:

Column 6, line 11, "233°" should read -- 223° --.

Column 6, line 28, claim 1, "$RS:(NR'_2)_3$" should read -- $RSi(NR'_2)_3$ --.

Column 6, line 57, claim 4, "catalyst" should read -- catalytic --.

Signed and Sealed this

Nineteenth Day of February 1980

[SEAL]

Attest:

SIDNEY A. DIAMOND

Attesting Officer     Commissioner of Patents and Trademarks